United States Patent
Fu et al.

(10) Patent No.: US 9,965,846 B2
(45) Date of Patent: May 8, 2018

(54) METHOD AND APPARATUS FOR DETECTING CRYSTAL ORIENTATION OF SILICON WAFER

(71) Applicant: Trina Solar Co., Ltd, Changzhou, Jiangsu (CN)

(72) Inventors: Shaoyong Fu, Jiangsu (CN); Zhen Xiong, Jiangsu (CN)

(73) Assignee: Trina Solar Co., Ltd, Changzhou, Jiangsu (CN)

( * ) Notice: Subject to any disclaimer, the term of this patent is extended or adjusted under 35 U.S.C. 154(b) by 0 days. days.

(21) Appl. No.: 15/303,386

(22) PCT Filed: May 13, 2014

(86) PCT No.: PCT/CN2014/077340
§ 371 (c)(1),
(2) Date: Oct. 11, 2016

(87) PCT Pub. No.: WO2015/154326
PCT Pub. Date: Oct. 15, 2015

(65) Prior Publication Data
US 2017/0039696 A1   Feb. 9, 2017

(30) Foreign Application Priority Data
Apr. 11, 2014   (CN) .......................... 2014 1 0146800

(51) Int. Cl.
*G06T 7/00* (2017.01)
*G01N 21/55* (2014.01)
(Continued)

(52) U.S. Cl.
CPC ........... *G06T 7/0004* (2013.01); *G01N 21/55* (2013.01); *G01N 21/84* (2013.01); *G06K 9/4661* (2013.01);
(Continued)

(58) Field of Classification Search
CPC ....... H01L 22/12; H01L 29/045; G01N 21/55; G01N 21/84; G01N 2021/8477;
(Continued)

(56) References Cited

U.S. PATENT DOCUMENTS

| 5,576,543 A | 11/1996 | Dingley |
| 6,177,285 B1 * | 1/2001 | Jantke ..................... H01L 22/12 216/2 |

(Continued)

FOREIGN PATENT DOCUMENTS

| CN | 102680444 A | 9/2012 |
| CN | 103151283 A | 6/2013 |

(Continued)

OTHER PUBLICATIONS

State Intellectual Property Office of The P.R. China, International Search Report issued in PCT/CN2014/077340, dated Dec. 15, 2014, 7 pages with English translation, State Intellectual Property Office of the P.R. China, Beijing, China.

(Continued)

*Primary Examiner* — Brenda C Bernardi
(74) *Attorney, Agent, or Firm* — Marshall & Melhorn, LLC

(57) ABSTRACT

A method and apparatus for detecting crystal orientation of a silicon wafer is proposed. The detection method uses a camera shooting device to irradiate the silicon wafer in a rotation manner in different angular directions and obtains the corresponding reflection intensities, based on which a reflection curve is drawn for a grain of interest in a polar coordinate system; normal directions of three or more faces of a regular octahedron of a grain <111> are determined by identifying a pixel brightness extreme value in the reflection curve, and then all normal vectors of the regular octahedron are calculated, so that a crystal orientation of the grain of (Continued)

interest may be calculated. The camera shooting device has a light source and one or more camera shooting probes.

20 Claims, 5 Drawing Sheets

(51) Int. Cl.
    *G01N 21/84*     (2006.01)
    *G06K 9/46*     (2006.01)
    *H04N 5/225*     (2006.01)
    *H01L 21/66*     (2006.01)
    *H01L 29/04*     (2006.01)

(52) U.S. Cl.
    CPC ............ *G06T 7/0024* (2013.01); *H01L 22/12* (2013.01); *H04N 5/2256* (2013.01); *H04N 5/2258* (2013.01); *G01N 2021/8477* (2013.01); *G06T 2207/10152* (2013.01); *G06T 2207/30148* (2013.01); *H01L 29/045* (2013.01)

(58) Field of Classification Search
    CPC .. H04N 5/2256; H04N 5/2258; G06T 7/0004; G06T 7/0024; G06T 2207/30148; G06T 2207/10152; G06K 9/4661
    See application file for complete search history.

(56) References Cited

U.S. PATENT DOCUMENTS

| | | | |
|---|---|---|---|
| 6,462,339 B1 * | 10/2002 | Michaluk | ............ C23C 14/3414 |
| | | | 250/307 |
| 6,589,362 B2 | 7/2003 | Haga | |
| 6,748,345 B2 | 6/2004 | Chou et al. | |
| 2009/0059216 A1 | 3/2009 | Shibata et al. | |

FOREIGN PATENT DOCUMENTS

| | | | | |
|---|---|---|---|---|
| DE | 19725535 A1 | 12/1998 | | |
| JP | 2000031245 A | 1/2000 | | |
| JP | 2001296258 A | 10/2001 | | |
| WO | WO-2011082677 A1 * | 7/2011 | ........... G01N 23/207 |
| WO | 2013/150424 A1 | 10/2013 | | |

OTHER PUBLICATIONS

Machine-Generated English Translation of DE 17525535, obtained via Espacenet Patent Search.

Extended European Search Report of PCT/CN2014/077340 (Dated.

* cited by examiner

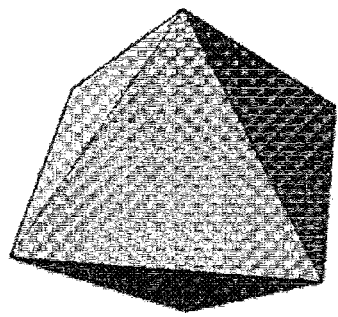 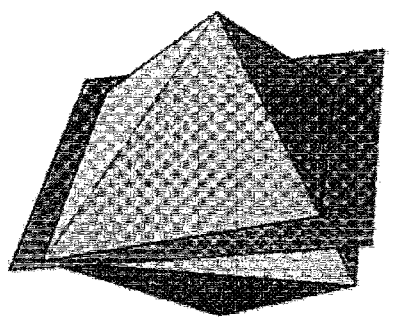
Fig. 3a　　　　Fig. 3b
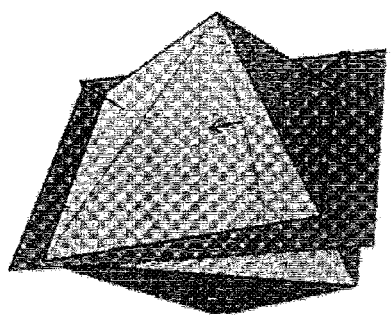 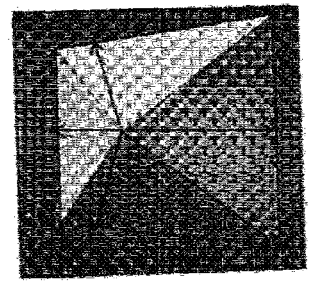
Fig. 3c　　　　Fig. 3d

| <100> | <110> | <111> | <124> | <205> | <113> | <122> |
|---|---|---|---|---|---|---|
| 35.9% | 3.6% | 27.5% | 8.5% | 7.6% | 0.4% | 16.5% |

METHOD AND APPARATUS FOR DETECTING CRYSTAL ORIENTATION OF SILICON WAFER

TECHNICAL FIELD

The present invention relates to a method and apparatus for detecting crystal orientation of a silicon wafer.

BACKGROUND ART

Grains of a solar ingot polysilicon wafer are generally sized at about 1 cm, and the number of grains of a single silicon wafer is more than 500. The grains are different due to their crystal orientations, and also have different effects on the subsequence battery processes. For example, a <100> crystal orientation may obtain, by alkali texturization, a pyramid textured surface with a high light-harvesting effect, while a <111> crystal orientation can obtain a textured surface only through acid texturization or other isotropic texturization ways. Different grains have different crystal orientations and different crystal orientations have different textured surface properties, which in turn result in different surface recombination rates, affecting performance parameters of the final battery. As such, proper detection and evaluation of the crystal orientations of the entire silicon wafer facilitates optimization of a fabricating process of the battery. However, depending on the current technology level, an effect of properly measuring the crystal orientations of the entire silicon wafer has not been achieved yet.

Currently, there are three major types of methods for measuring the crystal orientations:

1) X-ray diffraction (briefly referred to as XRD) technology, wherein its beam spot generally has a diameter of several millimeters (mm) and each time only a crystal orientation of a single grain of the silicon wafer can be measured. This is high in cost and very time consuming, and cannot fully satisfy requirements of the industry.

2) Electron backscattered selective diffraction (briefly referred to as EBSD) technology, which is suitable for detecting crystal orientation of a microdomain and may be used for surface scanning, wherein its spatial resolution may be up to 0.1 μm, but the range being measured is also limited to only several square centimeters (cm²), not suitable for quickly characterizing a full-size silicon wafer.

3) A rotating table reflection approach (CN103151283A, the entirety of which is incorporated into the present application by reference and acts as a part of the disclosure of the specification), which was proposed previously by the inventors of the present application. This technical solution can achieve crystal orientation calculation on a large-area sample. The rotating table reflection approach disclosed by CN103151283A has already possessed efficient industrial practicality. However, during its implementation, the applicant has further found the following aspect to be improved: its calculation method is a method to make comparison with a standard crystal orientation, which has a limited theoretical accuracy.

In view of the state of the art, there exists an urgent requirement in the current photovoltaic field to provide a technology for detecting the crystal orientation of the silicon wafer more quickly and accurately.

SUMMARY OF THE INVENTION

The present invention utilizes the nature that a crystal orientation of a silicon wafer would affect its surface morphology, which in turn leads to anisotropy of surface reflection ability of the silicon wafer. The present invention may use a CCD imaging technology to capture a relationship between a grain reflection intensity of a surface of the silicon wafer and a spatial angle, and in turn utilizes principles of optics and crystallography to calculate a crystal orientation corresponding to the grain.

The basic principle utilized by the present invention is: when the grain of the surface of the silicon wafer is being irradiated with a light source, the grain will reflect light. Usually, reflection intensities of the grain are different in various directions, i.e., anisotropy of the reflection ability appears. Upon research, the inventors have found that the main reason for the reflection intensities of a grain being different in various directions is because <111> close-packed faces of silicon are easier to retain during machining and corroding. With reference to FIG. 3a, eight <111> close-packed faces spatially form a regular octahedron. Consider an ideal case, it is assumed that for any grain on the silicon wafer, only the <111> faces can be exposed to the surface. Then, for a crystal face A of any crystal orientation, its pyramid shape will be shown as FIG. 3b. In a new coordinate system in which the surface of the silicon wafer is used as an XOY plane, vector representations of various <111> vectors are shown in FIG. 3c. The most intense value of its grain reflection curve will appear in a normal direction as shown in FIG. 4c, and its two-dimensional (2D) form is shown in FIG. 3d.

Based on the above premise, a theoretical calculation may be performed as follows: as long as three or more (including three) of the 2D normal directions in FIG. 3d have been obtained, the following equation group may be built to reconstruct a three-dimensional (3D) form of four normal vectors:

$$V_i \cdot V_j = \cos(\alpha_0) \cdot |V_i| \cdot |V_j|, \alpha_0 \text{ is } 70.53° \text{ or } 109.47°$$

$$i,j=\{1,2,3,4\}, i \neq j \quad \text{(Equation 1)}$$

In the above equation, $V_i$, $V_j$ represent normal vectors of faces of the regular octahedron. The characteristic angle $\alpha_0$ has a value that is an angle of two adjacent faces of the regular octahedron, which is a constant that can be obtained based on an objective lattice structure of silicon. In the above example, the value is accurate to the second decimal place, but higher or lower accuracy may also be available. By solving the above equation group and in conjunction with a symmetric property of crystal, all normal vectors of the regular octahedron may be calculated and thus a crystal orientation of each grain may be calculated. It also needs to be mentioned that due to symmetry of the regular octahedron, only four normal vectors need to be reconstructed with Equation 1.

Therefore, the present invention proposes a solution: using a camera shooting device (including a light source and one or more camera shooting probes) to irradiate the silicon wafer in a rotation manner in different angular directions and obtaining the corresponding reflection intensities, drawing a reflection curve for a grain of interest in a polar coordinate system based on said reflection intensities; determining normal directions of three or more faces of a regular octahedron of a grain <111> by identifying a pixel brightness extreme value in the reflection curve, and then calculating all normal vectors of the regular octahedron, so that a crystal orientation of the grain of interest may be calculated.

According to one aspect of the present invention, a method for detecting crystal orientation of a silicon wafer is proposed, comprising: a) with a camera device including a light source, photographing the silicon wafer positioned on a platform at different rotation angles, wherein after each photographing, said platform and said camera shooting device make a relative rotation about a main axis of said platform for an angle of α, and photographing is performed again, until images at n rotation angles have been obtained, wherein n=360/α; b) performing projection transformation and registration on the photographed images; c) for a grain on said silicon wafer, obtaining a pixel brightness on each image at the same position, and arranging the pixel brightness according to an accumulated rotation angle for the time of photographing, so as to obtain a grain reflection curve of said grain; d) within the gain reflection curve, identifying pixel brightness extreme values at three or more different shooting angles; e) determining normal directions of three or more faces of a <111> regular octahedron of the grain based on the determined pixel brightness extreme values; f) calculating all normal directions of the regular octahedron based on the determined normal directions of the three or more faces and in conjunction with a symmetric property of the regular octahedron of the grain; and g) determining a crystal orientation of said grain on the silicon wafer according to the calculated normal vectors of the regular octahedron.

According to one aspect of the present invention, in said step f) of the above solution, the following equation is solved based on the determined normal directions of the three or more faces:

$$V_i, V_j = \cos(\alpha_0) \cdot |V_i| \cdot |V_j|, i,j = \{1,2,3,4\}, i \neq j$$

wherein $V_i$, $V_j$ represent normal vectors of faces of the regular octahedron, $\alpha_0$ is an acute angle or an obtuse angle of adjacent faces of the <111> regular octahedron of the grain.

According to one aspect of the present invention, in the above solution, said camera shooting device comprises one or more imaging probes, and a main axis of said light source and the respective main axis of said one or more imaging probes are provided substantially in the same angular plane.

According to one aspect of the present invention, in the above solution, said camera shooting device comprises a first imaging probe and a second imaging probe, and a main axis of said light source, a main axis of said first imaging probe and a main axis of said second imaging probe are provided substantially in the same angular plane.

According to one aspect of the present invention, in the above solution, an angle θ1 between the main axis of said first imaging probe and a surface of the silicon wafer is 75°, and an angle θ2 between the main axis of said second imaging probe and the surface of the silicon wafer is 45°.

According to one aspect of the present invention, in said step a) of the above solution, a first set of n images and a second set of n images are obtained respectively with said first imaging probe and said second imaging probe, and in said step c), a first grain reflection curve is obtained based on the first set of n images and a second grain reflection curve is obtained based on the second set of n images.

According to one aspect of the present invention, in said step d) of the above solution, when pixel brightness extreme values are identified from the first grain reflection curve and the second grain reflection curve at the same shooting angle, a larger brightness is selected.

According to one aspect of the present invention, in the above solution, further comprising: determining an angle γ between an angular plane in which the first imaging probe is situated and an angular plane in which the second imaging probe is situated, and correcting one of the first grain reflection curve and the second grain reflection curve based on said angle γ.

According to one aspect, in said step c) of the above solution, said grain reflection curve is drawn in a polar coordinate, wherein a polar angle corresponds to an accumulated rotation angle for the time of photographing, and a polar radius corresponds to the pixel brightness.

According to one aspect of the present invention, in said step e) of the above solution, it is assumed that the pixel brightness extreme value occurs in a direction of vertical line on an exposed face of the <111> regular octahedron.

According to one aspect of the present invention, in the above solution, said light source is a diffuse reflection light source.

According to one aspect of the present invention, in the above solution, said light source is a LED panel light source.

According to one aspect of the present invention, in said step a) of the above solution, said camera shooting device is held still and said platform is rotated; or said platform is held still and said camera shooting device is rotated.

According to one aspect of the present invention, in the above solution, said silicon wafer is a polysilicon wafer, and said method comprising: performing steps c)-g) for each grain on the polysilicon wafer to determine its crystal orientation; classifying and counting a crystal orientation of individual grains according to the angle; and obtaining a crystal orientation distribution of the polysilicon wafer based on the counted result.

According to one aspect of the present invention, an apparatus for detecting crystal orientation of a silicon wafer is proposed, comprising: a platform for positioning the silicon wafer; a camera shooting device including a light source for photographing the silicon wafer positioned on said platform, wherein one of said platform and said camera shooting device may rotate about a main axis of said platform with respect to the other of said platform and said camera shooting device; an image processing device coupled to said camera shooting device; and a control unit for controlling said platform, said camera shooting device and said image processing device to implement any of the methods as described above.

According to one aspect of the present invention, a method for analyzing a crystal boundary type is proposed, said method comprising: performing any of the methods as described above on a silicon wafer to obtain a crystal orientation of a grain on a silicon wafer; and determining the crystal boundary type based on the calculated crystal orientation.

BRIEF DESCRIPTION OF THE DRAWINGS

The drawings are provided for further understanding of the present invention and they are incorporated herein to constitute a part of the application. The drawings illustrate embodiments of the present invention and are for the purpose of explaining the principles of the present invention along with the specification, in which:

FIG. 2d shows a reflection curve (polar coordinate system) at a certain point on a grain obtained according to the image of FIG. 2a;

FIG. 3a shows a regular octahedron spatially consisting of eight <111> close-packed faces, FIG. 3b shows an exemplary pyramid shape on any crystal face, FIG. 3c shows a position where the most intense value of a grain reflection curve appears, and FIG. 3d shows 2D representations of the normal directions in FIG. 3c;

DETAILED DESCRIPTION OF THE INVENTION

In the following description, the present invention is described with reference to various embodiments. However, those skilled in the art will recognize that these various embodiments may be practiced without one or more specific details or along with other alternative and/or additional method, material or component. In other conditions, well-known structures, materials or operations have not been shown or described in details so as not to obscure aspects of the various embodiments of the present invention. Similarly, for the purpose of explanation, particular number, material and configuration are set forth to provide complete understanding of the embodiments of the present invention. However, the present invention may be practiced without such specific details. In addition, it should be understood that the various embodiments as shown herein are illustrative representations and are not necessarily drawn to scale.

Exemplary Apparatus for Detecting Crystal Orientation

Figure 1:
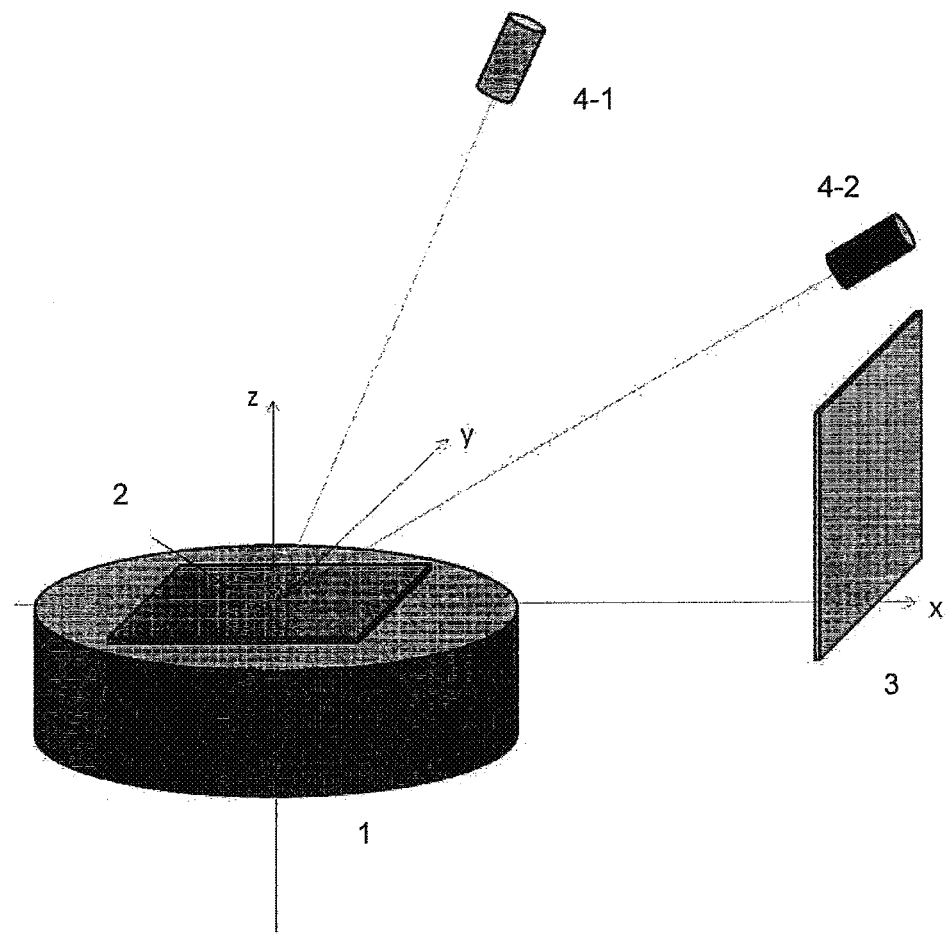
FIG. 1 shows an exemplary structure of an apparatus for detecting crystal orientation according to an embodiment of the present invention.

With reference to FIG. 1, an exemplary structure of an apparatus for detecting crystal orientation according to the present invention is shown. According to an embodiment of the present invention, an apparatus for detecting crystal orientation is provided, and it is generally provided within a darkroom. An inner wall of the darkroom may be a coarse black surface, preferably close to blackbody. This apparatus for detecting crystal orientation includes:

1) a horizontal rotating table 1 that may accurately control a rotation angle within 360°. A minimum resolution of the horizontal rotating table 1 may at least be 0.1°, for example, and its resolution decides the final accuracy of detecting the crystal orientation. A silicon wafer 2 may be positioned on the rotating table and may be rotated along with the rotating table.

2) a first imaging probe 4-1 and a second imaging probe 4-2, whose specifications may be, e.g., an industrial single-color image acquisition camera, having an image bit depth of 16 or more. The first imaging probe and the second imaging probe face toward a center of the horizontal rotating table 1 (usually, that is also a center of a silicon wafer to be measured).

An angle between a main axis of the first imaging probe 4-1 and a surface of the silicon wafer is θ1, and the main axis is crossed with the surface of the silicon wafer at a central point thereof. In this embodiment, a recommended value for θ1 is 75°, but θ1 may also be other suitable value. An angle between a main axis of the second imaging probe 4-2 and the surface of the silicon wafer is θ2 and the main axis is crossed with the surface of the silicon wafer at the central point thereof. In this embodiment, a recommended value for θ2 is 45°, but θ2 may also be other suitable value.

Assume that principle points of the imaging probes 4-1 and 4-2 are C1, C2. In an ideal case, C1, C2 and a rotation center O are all in an XOZ plane. The actual case is that installation cannot make a C1OZ plane and a C2OZ plane overlap completely and there is always a small angle γ between them. Since rotation accuracy of the rotating table may be very high (as described above, the minimum resolution may be 0.1°), during subsequent calculation, in a preferred case, this small angle γ needs to be taken into account, as a correction factor.

3) a light source 3. The light source 3 may have a parallel light, and may also be a diffuse reflection light source exemplified in the figure. In a preferred embodiment, a LED panel light source may be used, as it has stable brightness and no flicker. Reflection patterns of different light sources may have a certain difference, but this would not affect the final theoretical calculation.

In fact, a position of the diffuse reflection light source 3 does not need to be very accurate, and the sole requirement is to have intersecting lines with two planes of C1OZ, C2OZ. In a preferred case, a main axis of the light source 3, the main axis of the first imaging probe 4-1 and the main axis of the second imaging probe 4-2 are provided substantially in the same angular plane.

4) In some embodiments, the subject matters of the present invention encompass the above apparatus for detecting crystal orientation and a darkroom mechanism to be used with this apparatus.

Exemplary Method for Detecting Crystal Orientation

Figure 4:
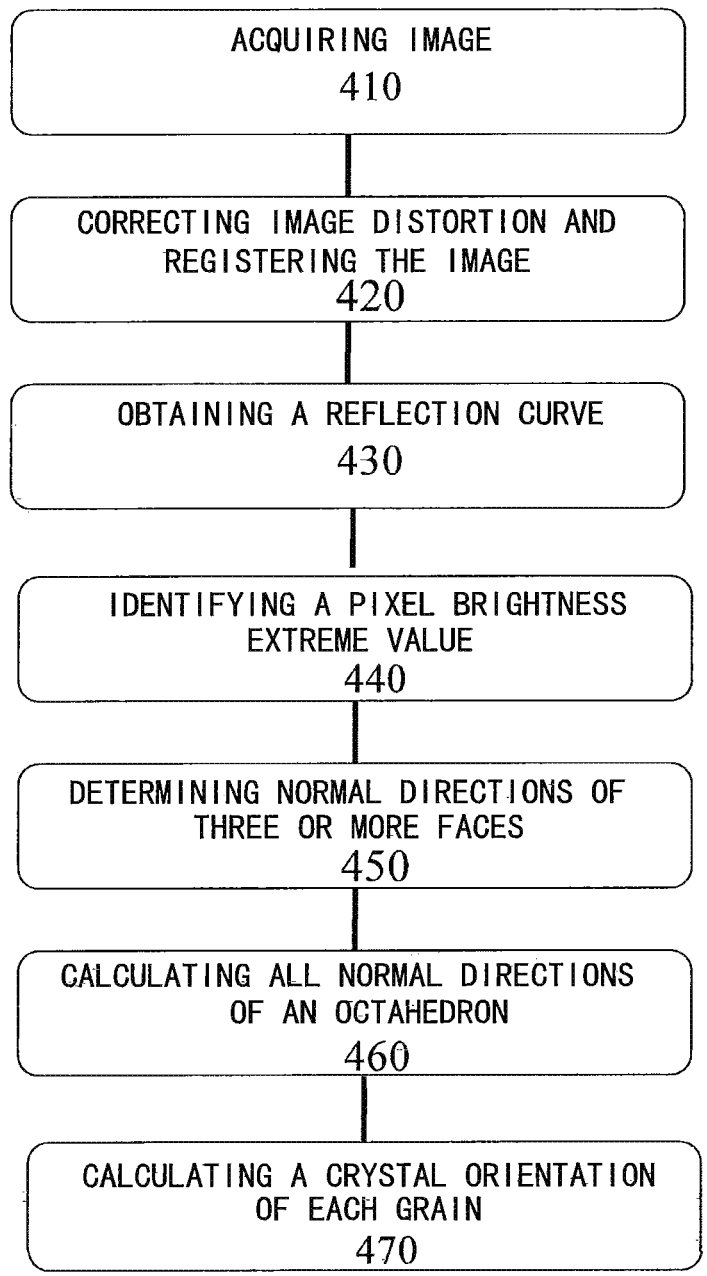
FIG. 4 shows an exemplary flow chart of a method for detecting crystal orientation according to an embodiment of the present invention.

According to an embodiment of the present invention, a crystal orientation of a grain of a surface of a silicon wafer may be detected by the apparatus for detecting crystal orientation as shown in FIG. 1. In conjunction with a flow chart in FIG. 4, an exemplary method is described as follows. It needs to be stated that, for the ease of better understanding, the following embodiments give many implementation details, but these technical details are only for the purpose of example and shall not constitute a limitation on the present invention. At the same time, it should be understood that not all the technical details are necessary to implement the present invention.

1) Preparing a silicon wafer: the silicon wafer may be a polysilicon wafer that is fabricated directly with a mortar line cutter, and this silicon wafer may also be placed in an alkali solution for alkali texturing for 1-10 minutes. The alkali texturing may make a reflected signal more acute, but this is not necessary to implement the present invention.

Figure 2A:
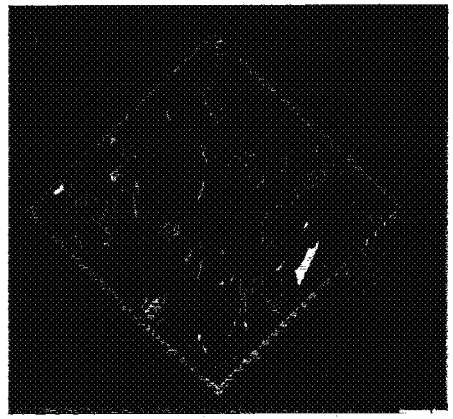
FIG. 2a shows an original image acquired by the apparatus of FIG. 1.

2) Acquiring images (410): every time the horizontal rotating table 1 rotates (e.g., rotates counterclockwise) for a certain angle α, a photo for the silicon wafer as shown in FIG. 2a is taken and an accumulated rotation angle φ of the rotating table for the time of taking the photo is identified.

$$\varphi = n \times \alpha$$

Wherein n is a total number of rotations. The rotation angle α is the resolution for calculating the crystal orientation, and generally needs to be less than or equal to 0.1°. Take a rotation angle of 0.1° as an example, upon rotation of one circle is completed, 3,600 photos of the silicon wafer with identification of accumulated angle would-be obtained. With respect to FIG. 2a, it also needs to be stated that the grain is relatively dark at most angles, only when it is at a characteristic angle, the grain will be very bright and has a large contrast with the periphery, this is shown as a highlighted part in the photo.

Figure 2B:
FIG. 2b shows an image after the original image has been registered.
Figure 2C:
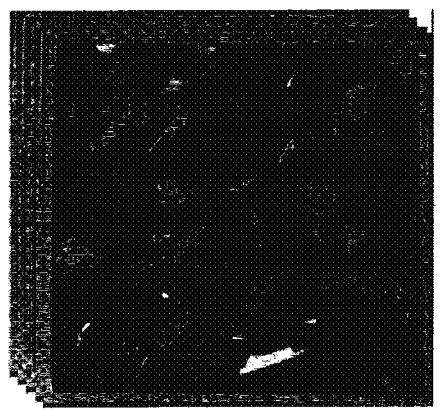
FIG. 2c shows a phantom image in which images of a silicon wafer are arranged.

3) Correcting image distortion and registering the image (420): since camera lens may have distortion, distortion correction according to inner and outer parameters of a camera is needed. Since the angles between the main-axes of the imaging probes 4-1 and 4-2 and the surface of the silicon wafer 2 are quite deviating from 90°, projection transformation and registration need to be performed on the taken photo, to convert it into a forward top view of FIG. 2b, and then subsequent calculation may be performed. Since the exemplary silicon wafer 2 is a regular square, after projection transformation, the image only needs to be rotated clockwise for $\varphi$ to complete registration.

Figure 2D:
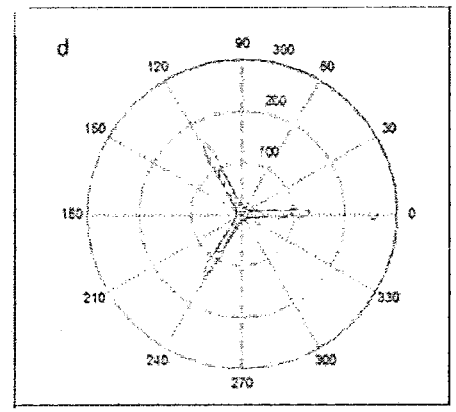

4) Obtaining a reflection curve (430): for each grain of interest, obtaining a brightness of the grain on the individual photographed images. For example, a point on the grain of interest is picked on the image, and its coordinate $(x_0, y_0)$ is returned. A brightness of a $(x_0, y_0)$ pixel point of each image I is retrieved, and arranged according to an accumulated rotation angle $\varphi$, so as to obtain an array $\sigma_n$, i.e., a grain reflection curve. $\sigma_n$ is drawn in a polar coordinate, as shown in FIG. 2d. The meaning of this reflection curve is to show light reflection intensities of the grain in different angular directions.

Since two imaging probes 4-1 and 4-2 are used in this embodiment, each image probe obtains a set of images. Two reflection curves can be obtained respectively according to the two sets of images. In addition, if the small angle $\gamma$ between the C1OZ plane and the C2OZ plane is not ignorable as compared to the rotation angle $\alpha$, one of the two reflection curves needs to be corrected with the angle $\gamma$.

5) Identifying a pixel brightness extreme value from the reflection curve (440): identifying the pixel brightness extreme value (representing the most intense grain reflection) and the corresponding rotation angle from the reflection curve obtained in step 4). The pixel brightness extreme value usually corresponds to a peak part in FIG. 2d. Since two reflection curves are obtained with two camera shooting probes in the preferred embodiment, a pixel brightness extreme value is identified in each reflection curve. As described above, since the pixel brightness extreme values at least three different rotation angles are needed, two camera shooting probes may be used to ensure that sufficient pixel brightness extreme values are photographed. If pixel brightness extreme values are identified from two reflection curves at the same rotation angle, a larger brightness may be selected.

6) Determining normal directions of three or more faces of a regular octahedron of the grain based on the determined pixel brightness extreme value (450);

7) Calculating all normal directions of the regular octahedron based on the determined normal directions of the three or more faces and in conjunction with a symmetric property of the regular octahedron of the grain (460); and 8) Determining a crystal orientation of the grain of interest based on the calculated normal vectors of the regular octahedron (470).

So far, the crystal orientation of the grain of interest has been obtained. If the silicon wafer to be measured is a polysilicon wafer, steps 4)-8) may be performed on each grain of the surface of the silicon wafer and the crystal orientation of individual grains may be classified according to the angle so as to obtain a crystal orientation distribution of the entire polysilicon wafer.

The serial number of the above steps of this method is only for the purpose of description, and does not mean the steps must to be implemented in this order. For example, acquiring the image in step 2) and correcting image distortion and registering the image in step 3) may be performed at the same time.

Variations of the Present Invention

The above method is only one of the various embodiments for implementing the present invention. Those skilled in the art should understand that the present invention has multiple variations.

Variation 1: in the above embodiments of apparatus and method for detecting crystal orientation, the camera shooting device includes two camera shooting probes. The use of two camera shooting probes may ensure that sufficient pixel brightness extreme values are photographed. However, the present invention also encompasses an embodiment in which only one camera shooting probe is used. In comparison with the solution with two camera shooting probes in the above embodiment, using one camera shooting probe may possibly reduce the recognition rate of the pixel brightness extreme value/normal direction. However, as described above, the present invention only needs to recognize three normal directions so that all normal vectors of the regular octahedron may be calculated. Thus, although a single camera shooting probe may somewhat compromise the recognition rate, it is still practical (a single-camera solution is intended to be encompassed herein).

Likewise, the variation of the present invention also encompasses a solution with multiple (more than three) camera shooting probes, which may further improve the recognition rate.

Variation 2: the present invention provides a quick and accurate crystal orientation detection result. Based on the detection result, there may be many extended applications, including: determining a crystal boundary type based on the detected crystal orientation.

Variation 3: in the above embodiments, the light source 3 and the camera shooting probes 4-1, 4-2 are fixed while the horizontal rotating table 1 may rotate. In contrast with this, it is also practical to use a fixed platform, and rotatable light source and probes. More specifically, as long as the platform and the light source make a relative rotation, they shall be within the scope of the present invention.

Meanwhile, the present invention encompasses the corresponding apparatus for crystal orientation detection. The exemplary crystal orientation detection apparatus according to the present invention may further comprise a specific controller for operating the horizontal rotating table 1, the light source 3, the probes 4-1, 4-2, so as to take the images of the polysilicon wafer according to the above method embodiments. The controller may also be equipped with the ability of performing digital processing (image distortion correction, image registration, reflection curve acquisition, pixel brightness extreme value identification, calculation of normal vectors of the octahedron, etc.) on the taken images to obtain a final detection result.

Experimental Example 1

Experimental Example 1 uses the method of the present invention for detecting a silicon wafer with a known standard crystal orientation to verify a detection accuracy of the method of the present invention. Steps and corresponding experimental data of Experimental Example 1 are given below.

1. A 1 cm×2 cm standard commercial small silicon wafer of <100> crystal orientation is placed in a KOH solution (with a volume concentration of 2.5%) for corroding for 3 minutes;

2. The silicon wafer is positioned on a rotating table and a rotation curve of the grain of interest is acquired, as shown in the block of FIG. 2a;

3. After the rotation curve has been obtained, an angle at which its extreme value is situated is obtained, and its (111) face normal vector is solved according to Equation (1), so that the obtained crystal orientation index vector of the grain is <0.99 0.012 0.021>, whose difference from a standard <100> crystal orientation angle is less than 1.5°.

Experimental Example 2

Experimental Example 2 uses the method of the present invention for detecting a entire surface of a polysilicon wafer to determine crystal orientation of individual grains so as to understand a crystal orientation distribution of the entire surface of the polysilicon wafer.

Experimental Example 2 and corresponding experimental data are given below.

Figure 5:
FIG. 5 shows a crystal orientation distribution of a polysilicon surface obtained by analyzing Experimental Example 2.

1. A polysilicon wafer cut by silicon carbide mortar is placed in a KOH solution (with a volume concentration of 2.5%) for corroding for 3 minutes;

2. The corroded silicon wafer is placed onto the apparatus in FIG. 1 for optical measurement, wherein a step angle of the rotating table is 0.1;

3. Reflection patterns of all the grains are obtained by a digital image processing method;

4. A crystal orientation is calculated for the reflection pattern according to Equation 1, so as to obtain accurate crystal orientations for all the grains. To facilitate the statistical, the individual crystal orientations are classified into 7 types according to the angles, so that a crystal orientation-distribution as shown in FIG. 5 and quantification statistics of the crystal orientation distribution as shown in Table 1 as follows may be obtained.

TABLE 1

| Ratios of the individual crystal orientations in Experimental Example 2 | | | | | | |
|---|---|---|---|---|---|---|
| <100> | <110> | <111> | <124> | <205> | <113> | <122> |
| 35.9% | 3.6% | 27.5% | 8.5% | 7.6% | 0.4% | 16.5% |

Technical Effects

The present invention utilizes optical imaging and digital image processing technologies to quantitatively analyze the anisotropic reflection rule of the polysilicon wafer, and combine the rule with a basic principle of crystallography, so that accurate crystal orientations of the grains in the silicon wafer may be calculated. According to different accuracies, the whole detection process lasts for about 10 minutes, so that the accuracies and rates are both improved in comparison with the prior art.

Several embodiments of the present invention have been described above. However, the present invention may be embodied as other specific forms without departing from its spirit or essential features. The described embodiments should be considered to be illustrative and not limitative in all aspects. As such, the scope of the present invention is defined by the accompanying claims, not by the above description. All changes which come within the meaning and scope of equivalency of the claims are to be embraced within the scope of the claims.

The invention claimed is:

1. A method for detecting crystal orientation of a silicon wafer, comprising:
   a) with a camera shooting device including a light source, photographing said silicon wafer positioned on a platform at different rotation angles, wherein after each photographing, said platform and said camera shooting device make a relative rotation about a main axis of said platform for an angle of a, and photographing is performed again, until images at n rotation angles have been obtained, wherein $n=360/\alpha$;
   b) performing projection transformation and registration on the photographed images;
   c) for a grain on said silicon wafer, obtaining a pixel brightness on each image at the same position, and arranging the pixel brightness according to an accumulated rotation angle for the time of photographing, so as to obtain a grain reflection curve of said grain;
   d) within said grain reflection curve, identifying pixel brightness extreme values at three or more different shooting angles;
   e) determining normal directions of three or more faces of a <111> regular octahedron of a grain based on the determined pixel brightness extreme values;
   f) calculating all normal directions of said regular octahedron based on the determined normal directions of said three or more faces and in conjunction with a symmetric property of said regular octahedron of said grain; and
   g) determining a crystal orientation of said grain on said silicon wafer according to the calculated normal vectors of said regular octahedron.

2. The method according to claim 1, wherein in said step f), solving the following equation based on the determined normal directions of said three or more faces:

$$V_i \cdot V_j = \cos(\alpha_0) \cdot |V_i| \cdot |V_j|, i,j=\{1,2,3,4\}, i \neq j$$

wherein $V_i$, $V_j$ represent a normal vectors of faces of said regular octahedron, and $\alpha_0$ is an acute angle or an obtuse angle of adjacent faces of said <111> regular octahedron of said grain.

3. The method according to claim 1, wherein said camera shooting device comprises one or more imaging probes, and a main axis of said light source and the respective main axis of said one or more imaging probes are provided substantially in the same angular plane.

4. The method according to claim 1, wherein said camera shooting device comprises a first imaging probe and a second imaging probe, and a main axis of said light source, a main axis of said first imaging probe and a main axis of said second imaging probe are provided substantially in the same angular plane.

5. The method according to claim 4, wherein an angle θ1 between said main axis of said first imaging probe and a surface of said silicon wafer is 75°, and an angle θ2 between said main axis of said second imaging probe and said surface of said silicon wafer is 45°.

6. The method according to claim 4, wherein in said step a), a first set of n images and a second set of n images are obtained respectively with said first imaging probe and said second imaging probe, and in said step c), a first grain reflection curve is obtained based on said first set of n images and a second grain reflection curve is obtained based on said second set of n images.

7. The method according to claim 6, wherein in said step d), when pixel brightness extreme values are identified from said first grain reflection curve and said second grain reflection curve at the same shooting angle, a larger brightness is selected.

8. The method according to claim 4, further comprising: determining an angle γ between an angular plane in which said first imaging probe is situated and an angular plane in which said second imaging probe is situated, and correcting one of said first grain reflection curve and said second grain reflection curve based on said angle γ.

9. The method according to claim 1, wherein in said step c), said grain reflection curve is drawn in a polar coordinate, wherein a polar angle corresponds to a accumulated rotation angle for the time of photographing, and a polar radius corresponds to said pixel brightness.

10. The method according to claim 1, wherein in said step c), it is assumed that said pixel brightness extreme value occurs in a direction of vertical line on an exposed face of the <111> octahedron.

11. The method according to claim 1, wherein said light source is a diffuse reflection light source.

12. The method according to claim 1, wherein said light source is a LED panel light source.

13. The method according to claim 1, wherein said relative rotation in said step a) is either:
holding said camera shooting device still and rotating said platform; or
holding said platform still and rotating said camera shooting device.

14. The method according to claim 1, wherein said silicon wafer is a polysilicon wafer, said method comprising:
performing steps c)-g) for each grain on said polysilicon wafer to determine its crystal orientation;
classifying and counting a crystal orientation of individual grains according to the angle; and
obtaining a crystal orientation distribution of said polysilicon wafer based on the counted result.

15. An apparatus for detecting crystal orientation of a silicon wafer, comprising:
a platform for positioning said silicon wafer;
a camera shooting device including a light source for photographing said silicon wafer positioned on said platform, wherein one of said platform and said camera shooting device may rotate about a main axis of said platform with respect to the other of said platform and said camera shooting device;
an image processing device coupled to said camera shooting device; and
a control unit for controlling said platform, said camera shooting device and said image processing device, said control unit to:
a) with the camera shooting device, photograph said silicon wafer positioned on a platform at different rotation angles, wherein after each photographing, said platform and said camera shooting device make a relative rotation about a main axis of said platform for an angle of a, and photographing is performed again, until images at n rotation angles have been obtained, wherein n=360/α;
b) perform projection transformation and registration on the photographed images;
c) for a grain on said silicon wafer, obtain a pixel brightness on each image at the same position, and arranging the pixel brightness according to an accumulated rotation angle for the time of photographing, so as to obtain a grain reflection curve of said grain;
d) within said grain reflection curve, identify pixel brightness extreme values at three or more different shooting angles;
e) determine normal directions of three or more faces of a <111> regular octahedron of a grain based on the determined pixel brightness extreme values;
f) calculate all normal directions of said regular octahedron based on the determined normal directions of said three or more faces and in conjunction with a symmetric property of said regular octahedron of said grain; and
g) determine a crystal orientation of said grain on said silicon wafer according to the calculated normal vectors of said regular octahedron.

16. The apparatus according to claim 15, wherein said control unit is to solve the following equation based on the determined normal directions of said three or more faces:

$$V_i \cdot V_j = \cos(\alpha_0) \cdot |V_i| \cdot |V_j|, i,j=\{1,2,3,4\}, i \neq j$$

wherein $V_i$, $V_j$ represent a normal vectors of faces of said regular octahedron, and α0 is an acute angle or an obtuse angle of adjacent faces of said <111> regular octahedron of said grain.

17. The apparatus according to claim 15, wherein said camera shooting device comprises one or more imaging probes, and a main axis of said light source and the respective main axis of said one or more imaging probes are provided substantially in the same angular plane.

18. The apparatus according to claim 15, wherein said camera shooting device comprises a first imaging probe and a second imaging probe, and a main axis of said light source, a main axis of said first imaging probe and a main axis of said second imaging probe are provided substantially in the same angular plane.

19. The apparatus according to claim 18, wherein an angle θ1 between said main axis of said first imaging probe and a surface of said silicon wafer is 75°, and an angle θ2 between said main axis of said second imaging probe and said surface of said silicon wafer is 45°.

20. The apparatus according to claim 15, wherein said light source is one of a diffuse reflection light source and a LED panel light source.

* * * * *